United States Patent [19]

Martan

[11] 4,058,566
[45] Nov. 15, 1977

[54] SEPARATION OF ISOMERS OF PHENOLS AND PHENOLIC ETHERS

[75] Inventor: Michael Martan, Skokie, Ill.

[73] Assignee: UOP Inc., Des Plaines, Ill.

[21] Appl. No.: 719,648

[22] Filed: Sept. 1, 1976

[51] Int. Cl.$^2$ .............................................. C07C 45/24
[52] U.S. Cl. .................................................. 260/600 R
[58] Field of Search ..................................... 260/600 R

[56] References Cited

PUBLICATIONS

Adams et al., Organic Reactions, vol. VIII, (1954), pp. 199-201, 205-215.

*Primary Examiner*—Bernard Helfin
*Attorney, Agent, or Firm*—James R. Hoatson, Jr.; Raymond H. Nelson; William H. Page, II

[57] ABSTRACT

Mixtures of isomeric ortho and para alkylated phenols or phenolic ethers may be separated without extensive distillation by treating a mixture of the isomers with a polyalkylene polyamine such as hexamethylenetetramine in the presence of a protonic solvent at sub-ambient temperatures.

7 Claims, No Drawings

SEPARATION OF ISOMERS OF PHENOLS AND PHENOLIC ETHERS

This invention relates to a process for the separation of isomers of alkylated phenols or phenolic ethers. More specifically, the invention is concerned with a process for separating ortho and para alkylated phenols or phenolic ethers utilizing a polyalkylene polyamine in the presence of a protonic solvent.

Alkylated phenols and phenolic ethers will find a wide variety of uses in the chemical field. For example, a chloromethylated anisole is used as an intermediate in the synthesis of anisic aldehyde. This compound, and particularly the para isomer, is used as an ingredient in perfume compositions which are in turn used as aroma components in the manufacture of perfumes, colognes, talcs, soaps, etc. In addition, para-anisic aldehyde is also used as an intermediate in the preparation of antihistamines and electroplating products. When subjecting phenol or phenolic ethers such as anisole to chloromethylation, the product which results from the chloromethylation step consists of a mixture of the ortho and para isomers. The separation of these isomers and particularly the separation of ortho-chloromethylanisole and para-chloromethylanisole is difficult to effect. The separation therefore requires rather extensive and expensive equipment thus making it rather prohibitive in cost when utilizing the equipment on an industrial scale. However, it has now been discovered that the two isomers may be separated in a relatively inexpensive and economical manner utilizing a process hereinafter set forth in greater detail.

It is therefore an object of this invention to provide a simple method for the separation of isomeric alkylated phenols or phenolic ethers.

A further object of this invention is to provide a process for separating para alkylated phenols or phenolic ethers from othro alkylated phenols or phenolic ethers utilizing a polyalkylene polyamine in the presence of a protonic solvent.

In one aspect an embodiment of this invention resides in a process for the separation of a mixture of isomeric ortho and para alkylated phenols or phenolic ethers which comprises treating said mixture with a polyalkylene polyamine in the presence of a protonic solvent at subambient temperatures, and recovering the desired isomer.

A specific embodiment of this invention is found in a process for the separation of a mixture of ortho-chloromethylanisole and para-chloromethylanisole by treating said mixture with hexamethylenetetramine in the presence of a protonic solvent comprising at a temperature in the range of from about 0° to about 20° C. and recovering the desired para-anisic aldehyde.

Other objects and embodiments will be found in the following further detailed description of the present invention.

As hereinbefore set forth the present invention is concerned with a process for separating various isomers of alkylated phenols and phenolic ethers. The process is effected by treating a mixture of the isomers with a polyalkylene polyamine such as hexamethylenetetramine in the presence of a protonic solvent by utilizing a reaction mixture comprising the isomeric alkylated phenolic ethers or phenols. With the hexamethylenetetramine, it is possible to isolate the desired isomer when using the protonic solvent. Solvents which are non-protonic in nature will be ineffective for accomplishing this purpose as will hereinafter be shown in greater detail. The separation process is effected in subambient temperatures and preferably temperatures which lie within a range of from about 0° to about 20° C.

Examples of alkylated phenols and phenolic ethers which may be subjected to the separation process of the present invention will include o-chloromethylphenol, p-chloromethylphenol, o-chloroethylphenol, p-chloroethylphenol, o-chloromethylanisole (o-chloromethyl phenylmethyl ether), p-chloromethylanisole, o-chloromethylphenetole, p-chloromethylphenetole, o-chloromethyl propylphenyl ether, p-chloromethyl propylphenyl ether, o-chloromethyl butylphenyl ether, p-chloromethyl butylphenyl ether, o-chloroethylanisole, p-chloroethylanisole, o-chloroethylphenetole, p-chloroethylphenetole, etc. It is to be understood that the aforementioned alkylated penols and phenolic ethers are only representative of the class of compounds which may be used as the starting material in the separation process of this invention, and that said invention is not necessarily limited thereto.

Examples of protonic solvents which may be employed to effect the separation process will include water, lower molecular weight aliphatic alcohols such as methyl alcohol, ethyl alcohol, n-propyl alcohol, isopropyl alcohol, n-butyl alcohol, etc.; carboxylic acids such as formic acid, acetic acid, propionic acid, butyric acid; or mixtures of these solvents such as water and methyl alcohol, water and ethyl alcohol, water and acetic acid, etc.

The process of this invention may be effected in any suitable manner and may comprise either a batch or continuous type operation. For example, when a batch type operation is employed, the mixture of isomeric compounds along with the protonic solvent and the polyalkylene polyamine such as hexamethylenetetramine is placed in an appropriate apparatus such as a flask which is provided with external cooling means. These external cooling means may comprise an ice bath, cooling coils, or any other apparatus known in the art. After subjecting the mixture to continuous stirring for a residence time which may range from about 0.1 up to about 1 hour or more in duration, stirring is discontinued and the mixture allowed to settle. The imine salt of the alkylated phenol or phenolic ether will precipitate out during the reaction and after settling will be separated from the organic layer. This imine salt which precipitates out will comprise the para isomer of the desired product while the ortho isomer will remain in soluble form in the organic layer. After separating the two layers by decantation, the solid imine salt is decomposed by conventional means to form the desired para aldehyde compound.

It is also contemplated within the scope of this invention that the separation process may be effected in a continuous type of operation. When this type of operation is employed the components of the reaction comprising the mixture of isomeric alkylated phenols or phenolic ethers are continuously charged to a reaction zone which is maintained at the proper operating conditions of temperature and pressure. In addition, the protonic solvent such as water, methyl alcohol, ethyl alcohol or mixtures thereof and the hexamethylenetetramine are continuously charged to this reactor through separate lines. If so desired, the protonic solvent and the hexamethylenetetramine may be admixed prior to entry into said reactor and the resulting mixture charged thereto in a single stream. After passage through the reactor for a predetermined residence time, the reactor effluent is continuously withdrawn and passed to a settling vessel. After the solid imine salt of the para isomer of the starting material has settled out, the liquid is removed by decantation, siphoning or any other means known in the art and the solids are withdrawn. These solids are then subjected to a decomposition process whereby the desired para aldehydic compound is recovered.

The following examples are given to illustrate the separation process of the present invention. However, it is to be understood that these examples are given merely for purposes of illustration and that the present invention is not necessarily limited thereto.

EXAMPLE I

Chloromethylanisole was prepared by placing 162 grams (1.5 mole) of anisole and 150 grams of toluene in a 1-liter round bottom flask which was equipped with a mechanical stirrer, thermowell and gas inlet. The gas inlet was connected by means of a glass tube to a 200 cc round bottom flask also equipped with a gas inlet and thermowell. The glass tube which extended from the smaller flask to the larger flask was surrounded by a heating tape. The 200 cc round bottom flask was charged with 64 grams (2.1 mole) of paraformaldehyde following which the flask was then heated and maintained at a temperature of 120° C. Hydrogen chloride gas was passed at a flow rate of from 200 to 300 cc/min. into the flask containing the anisole and toluene. Likewise, the depolymerized formaldehyde was also passed to the flask containing anisole and toluene at a rate which was sufficient to match the rate of hydrogen chloride addition and also at a rate which was sufficient to prevent repolymerization of the formaldehyde to paraformaldehyde. At the end of 4 hours, the hydrogen chloride gas flow was reduced to 20 ml/min. and thereafter was halted. The reaction product was recovered and subjected to gas-liquid chromatographic analysis which disclosed a 91% conversion of the anisole with a 96.7% selectivity to monochloromethylanisoles.

Upon completion of the chloromethylation process, a sufficient amount of distilled water was added to make 1:1 ratio of water to organic mixture. The temperature of the reaction mixture was lowered to about 10° C. by means of an ice bath following which solid hexamethylenetetramine was added in 3 incremental portions of about 0.2 mole of hexamethylenetetramine per mole of chloromethylated anisole during a period of 20 minutes. Upon completion of the addition of the hexamethylenetetramine the water layer was separated from the organic layer. The water layer was then heated to reflux temperature for a period of 1 hour. At the end of this time, the water layer was extracted with 2 portions of 50 cc of toluene and the toluene extract was added to the organic layer. Gas-liquid chromatographic analysis disclosed the formation of p-anisic aldehyde which had a purity of 92%.

In contradistinction to this, when the slow addition of hexamethylenetetramine to the water-organic mixture was omitted, the ratio of ortho-anisic aldehyde to para-anisic aldehyde was 30:70. It is therefore readily apparent that the addition of hexamethylenetetramine to the reaction mixture in which water was present as a protonic solvent the obtention of the desired para isomer was greatly increased.

EXAMPLE II

In this example anisole was subjected to chloromethylation in a manner similar to that set forth in the above examples. After preparation of the chloromethylated anisole, it was then treated with 200 cc of water which contained 5% sodium chloride. The mixture was then cooled to a temperature of about 10° C. and maintained in a range of from 10°-15° C. by means of an ice bath while 0.5 molar hexamethylenetetramine was slowly added to the chloromethylated anisole. Upon completion of the addition, the reaction mixture was subjected to separation whereby the water layer was separated from the organic layer. The water layer was then refluxed for a period of 1 hour and the para-anisic aldehyde in a yield of 99% was recovered. The organic layer which contained unreacted chloromethylated anisole was again treated with an additional amount of water and hexamethylenetetramine at a reduced temperature of 10° C. in a manner similar to that set forth above. The reaction mixture was then treated in a manner similar to that set forth above and it was determined that the anisic aldehyde which was recovered from this second treatment possessed a distribution of 40% o-anisic aldehyde and 60% p-anisic aldehyde. The 99% pure para-anisic aldehyde may be used in perfume compositions and may be used for the synthesis of drug intermediates while the mixture of 40% ortho-anisic aldehyde and 60% para-anisic aldehyde may be used for electroplating purposes in which a high ortho isomer may be tolerated.

EXAMPLE III

In this example chloromethylphenol is prepared by treating 100 grams of phenol and 250 grams of toluene in a 1-liter round bottom flask with hydrogen chloride gas which is passed into the flask at a flow rate of 200-300 cc/min. at 0° C. The mixture of phenol and toluene is also treated with depolymerized formaldehyde resulting from heating paraformaldehyde at a temperature of 120° C. and passing the depolymerized formaldehyde into the flask containing the phenol and toluene at a rate sufficient to match the rate of the hydrogen chloride addition and also at a rate sufficient to prevent repolymerization of the formaldehyde to paraformaldehyde. The resulting chloromethylphenols are recovered and 100 cc of water is added to the isomeric chloromethylphenol mixture. The mixture of isomeric chloromethylphenols and water is maintained at a temperature of from 10° to 15° C. by means of an ice bath while 50 grams of hexamethylenetetramine were charged in incremental portions during a period of 20 minutes to the mixture. Upon completion of the addition of the hexamethylenetetramine, the reaction mixture was recovered and the water layer was separated from the organic layer. The water layer was then heated to reflux and maintained thereat for a period of 1 hour. At the end of the 1 hour, the reaction mixture was analyzed and found to contain 97% of p-hydroxybenzaldehyde.

When an isomeric chloromethylphenol mixture is treated with hexamethylenetetramine in a manner similar to that set forth in the above paragraph using other protonic solvents such as methyl alcohol, acetic alcohol, or mixtures of water alcohols such as ethyl alcohol, the conversion of the mixture to the corresponding hydroxybenzaldehydes will result in the obtention of a relatively high percentage of the desired para isomer.

I claim as my invention:

1. A process for the separation by selective reaction of a mixture of ortho-chloromethylanisole and para-chloromethylanisole or a mixture of o-chloromethylphenol and p-chloromethylphenol, which comprises treating the mixture with hexamethylenetetramine in the presence of a protonic solvent at a temperature of from about 0° to about 20° C., and recovering the separated p-anisic aldehyde or p-hydroxybenzenaldehyde.

2. The process as set forth in claim 1 in which said mixture comprises ortho-chloromethylanisole and para-chloromethylanisole.

3. The process as set forth in claim 1 in which said mixture comprises o-chloromethylphenol and p-chloromethylphenol.

4. The process as set forth in claim 1 in which said protonic solvent is water.

5. The process as set forth in claim 1 in which said protonic solvent is a mixture of water and methyl alcohol.

6. The process as set forth in claim 1 in which said protonic solvent is a mixture of water and acetic acid.

7. The process as set forth in claim 1 in which said protonic solvent is a mixture of water and ethyl alcohol.

* * * * *